United States Patent

Talke et al.

Patent Number: 5,641,506
Date of Patent: Jun. 24, 1997

[54] MEDICAL PATCH MATERIAL AND A PROCESS FOR ITS PRODUCTION

[75] Inventors: Volker Talke, Reppenstedt; Karin Ludwig, Nuewied; Karl-Heinz Reinhold, Hausen; Kurt Seeger, Neuwied, all of Germany

[73] Assignee: Lohmann GmbH & Co., KG, Neuwied, Germany

[21] Appl. No.: 532,742
[22] PCT Filed: Mar. 7, 1994
[86] PCT No.: PCT/EP94/00669
§ 371 Date: Dec. 20, 1995
§ 102(e) Date: Dec. 20, 1995
[87] PCT Pub. No.: WO94/21206
PCT Pub. Date: Sep. 29, 1994

[30] Foreign Application Priority Data

Mar. 18, 1993 [DE] Germany ............ 43 08 649.7

[51] Int. Cl.$^6$ ............ A61F 13/02; A61L 15/16; A61K 9/70
[52] U.S. Cl. ............ 424/443; 424/448; 424/449
[58] Field of Search ............ 424/448, 449, 424/443

[56] References Cited

U.S. PATENT DOCUMENTS

| | | | |
|---|---|---|---|
| 4,645,502 | 2/1987 | Gale et al. | 604/896 |
| 4,911,916 | 3/1990 | Cleary | 424/449 |
| 5,133,972 | 7/1992 | Ferrini et al. | 424/449 |
| 5,262,165 | 11/1993 | Govil et al. | 424/448 |

*Primary Examiner*—Thurman K. Page
*Assistant Examiner*—Kathryne E. Shelborne
*Attorney, Agent, or Firm*—Wenderoth, Lind, & Ponack

[57] ABSTRACT

A medical patch material has a support coated with an even and porous spread of pressure sensitive hot-melt adhesive coating, formed by means of gravure printing, has a sufficient porosity and a resulting vapor permeability to skin moisture on the one hand, as well as an absolute bacteria-impermeability and reliable adherence of the patch material on the other hand. This is achieved by the fact that the pressure sensitive hot-melt adhesive spread:

a) forms coherent webs in the lengthwise and transverse direction, which include island-shaped adhesive-free areas;

b) that the proportion of the adhesive-free areas amounts to between 30 and 60%, preferably between 40 and 57% of the total surface, and c) that the coat weight of the adhesive amounts to between 30 and 160 g/m$^2$, preferably between 40 and 120 g/m$^2$.

16 Claims, No Drawings

MEDICAL PATCH MATERIAL AND A PROCESS FOR ITS PRODUCTION

The present invention relates to a medical patch material having a support coated with an even and porous spread of a pressure sensitive hot-melt adhesive, and to a process for its production.

According to the art, medical patch materials are composed of supporting materials of textile fabrics and/or films which are coated with adhesive substances of the group of natural rubber, synthetic rubber, polyvinyl ether, and polyacrylate copolymers based on solvents or dispersions.

Among these adhesive masses, natural rubber adhesives are disadvantageous because of their high allergization risk and their low aging resistance; for this reason their medical application has increasingly receded into the background. Dispersion adhesive masses have the disadvantage that solubilization of the adhesive masses occurs because of their low moisture resistance, therefore they too did not succeed in the market. The solvent acrylate adhesives, widely used today, have the disadvantage that the employed solvent has to be evaporated under heavy power and technical expenditure and must then be burnt or even recovered and directed to waste disposal.

Modern pressure sensitive hot-melt adhesives of synthetic-rubber adhesives based on block copolymers have not gained importance in the market until today, because their low permeability to water vapor prevents reliable, long-term adhesion on the human skin which releases about 500 $g/m^2/24$ h of water in state of rest.

Increasing the water-vapor permeability in a medical patch material by means of a porous spread, for example by using screen printing coaters, has been known for some time for the medicinal application of patch materials. However, the disadvantage of patch materials coated in this manner, wherein the adhesive is applied only in the form of islands and not coherently, lies in the fact that the film patches thus manufactured cannot ensure impermeability to bacteria, and that individual threads tend to unravel in case of textile fabrics. This not only concerns the optical impression but this sometimes renders reliable application impossible in case of elastic supporting materials.

Moreover, pressure sensitive hot-melt adhesives applied by means of screen printing have the property of giving a hemispherical spread and not a cylindrical one. In direct coating this results in the fact that the adhesive surface facing the skin, as compared with the applied adhesive amount, is very small and depends on the application pressure; and in transfer coating, the adherence to the supports is insufficient even if the lamination pressure is high. On the other hand, pressure sensitive hot-melt adhesive coatings having a coherent adhesive substance and tack-free spots arranged in the form of islands, provided that these were formed by means of gravure printing, failed to gain importance in the medical application because spreads of only up to 30 $g/m^2$ could be achieved by means of gravure coating. If higher spreads were applied, the fine structures achieved were unsatisfactory and the required porosity reduced to a considerable extent. In addition, these comparatively thin spreads resulted in low internal elasticity which was not sufficient to compensate surface differences between the human skin and the supporting material, which were caused by movements. Therefore the edges of the patch material frequently peeled in case of small spread amounts.

It is the object of the present invention to provide a medical patch material having a support coated with an even and porous spread of a pressure sensitive hot-melt adhesive and a process for its production. This makes it possible—by avoiding the above discussed disadvantages and technical limitations—to coat pressure sensitive hot-melt adhesives based on block copolymers having a suitable viscosity by means of gravure printing on supports of textile fabrics and/or films or foils in such a manner that with sufficient porosity the amount of adhesive applied is sufficient to ensure a reliable and permanent adherence of the patch materials on the human skin even in case of movements.

To achieve this object in a medical patch material having a support coated with an even and porous spread of a pressure sensitive hot-melt adhesive, the present invention proposes that the pressure sensitive hot-melt adhesive applied by means of a direct gravure coater is arranged on the supporting material such that a) it forms coherent webs in the longitudinal and transverse direction, which include island-shaped areas which are free from adhesive;

b) the proportion of the adhesive-free areas amounts to between 30 and 60%, preferably between 40 and 57% of the total surface, and c) the coat weight of the adhesive is between 30 and 160 $g/m^2$, preferably between 40 and 120 $g/m^2$.

Applying a pressure sensitive hot-melt adhesive based on block copolymers with suitable viscosity on the above-mentioned supporting materials in the manner according to the present invention advantageously results in the fact that the drawbacks of screen printing do not occur, that a thoroughly satisfactory porosity of the dry areas of between 30 and 60% is achieved, and that a reliable adhesion of the patch material on the human skin is ensured even in case of surface differences and resulting tensions caused by movements.

According to an advantageous embodiment, the adhesive-free islands regularly arranged in the pressure sensitive hot-melt adhesive have a maximum distance of 3 mm to one another. To this end, an embodiment provides that the base of the applied adhesive webs has a maximum width of 3 mm on the supporting material.

According to an embodiment, the pressure sensitive hot-melt adhesive is a block copolymer having a viscosity at 120° to 180° C. of between 1,000 and 20,000 mPa.s, preferably between 2,000 and 10,000 mPa.s.

According to an embodiment, the supporting material is a textile fabric. Such a textile fabric has a comparatively high porosity which is adjustable by the textile structure. The support may also be a vapor-permeable film.

According to an embodiment, the patch material has a water-vapor permeability of more than 2,000 $g/m^2/24$ h.

The medical patch material may be an adhesive patch, a patch-type bandage, an adhesive dressing, a securing patch, an allergy-test patch, or a bacteria-proof wound dressing.

The adhesive-coated support may also be an adhesive material which can be used in fields other than medicine, for example, self-adhesive tapes, labels etc. In these cases up to 50% of adhesive can be saved as compared to adhesive materials coated on the complete surface.

It is further provided that the patches according to the present invention are sterilizable. This may be achieved by radiation or ethylene oxide in a manner known to the skilled artisan.

A process for the production of the patch material according to the present invention provides that a textile fabric and/or a vapor-permeable film is coated with a pressure sensitive hot-melt adhesive based on block copolymers by means of a heatable direct gravure coater, which is knife-coated both with a rigid and an elastic knife in the adhesive take-up, in such a porous manner that the adhesive mass forms coherent webs in the lengthwise and cross direction, which include adhesive-free, island-shaped areas having a distance of up to 3 mm to one another, the proportion of adhesive-free areas amounting to between 30 and 60% and preferably between 40 and 57% of the total surface and the base of the adhesive webs having a maximum width of 3 mm, and that the patch material has a permeability to water vapor of at least 2,000 g/m²/24 h. The water-vapor permeability is determined at 40° C. and a difference of the relative air humidity of 80%.

According to an embodiment, the adhesive substance is applied to the support at a coat weight of between 30 and 160 g/m², preferably between 40 and 120 g/m².

Finally, it is provided that a block copolymer having a viscosity at 120° to 180° C. of between 1,000 and 20,000 mPa.s, preferably between 2,000 and 10,000 mPa.s is used as adhesive.

The present invention will be illustrated in greater detail in the following two examples:

EXAMPLE 1

A 50 μm siliconized polyester film of Daubert is coated at a coating temperature of 140° C. with 60 g/m² of the pressure sensitive hot-melt adhesive Lunamelt PS 3785 having a viscosity at 150° C. of 13,740 mPa.s; coating is carried out by means of a heatable direct gravure print coater whose engraved printing roll has a regular diamond-shaped pattern having a depth of 100 μm and wherein the dry areas arranged at a distance of 1.3 mm take 50% of the total surface. Immediately after coating, a 25 μm polymer film of ACE is laminated thereon under a pressure of 2 bar, said film having a water-vapor permeability of 4,400 g/m²/24 h when uncoated. The film thus coated has a permeability to water vapor of 2,500 g/m²/24 h and is impermeable to bacteria. The peel adhesion of the samples manufactured into wound dressings and γ-sterilized amounts to 15N/25 mm according to AFERA 4001. In wearing tests on the back of 10 test persons, the wound dressings show a reliable adhesion over 24 hours.

EXAMPLE 2

The polyester film of Example 1 is coated with 95 g/m² of the pressure sensitive hot-melt adhesive H 2322 H01 of Findley Adhesives Inc. having a viscosity at 177° C. of 7,800 mPa.s; coating is carried out with a gravure roll whose adhesive-free area amounts to 44% of the total surface and which consists of regular hexagons and has a depth of 140 μm. Immediately after coating, a crosswise elastic patch material of TEN CATE MEDICAL B.V. is laminated thereon under a pressure of 4 bar. After manufacture into adhesive dressings no unraveling of the patch edges can be observed even in case of stretching. In wearing tests the patches reliably stuck to the lower arms of 10 test persons over 24 hours. The water-vapor permeability of the patches amounted to 4,500 g/m²/24 h.

We claim:

1. Medical patch material having a support coated with an even and porous spread of a pressure-sensitive adhesive in such a manner that
    a) it forms coherent webs in the lengthwise and transverse direction, which include island-shaped adhesive-free areas; and
    b) the proportion of the adhesive-free areas amounts to between 30 and 60% of the total surface, and wherein
        (1) the pressure-sensitive adhesive is a pressure sensitive hot-melt adhesive based on block copolymers having a viscosity at 120° to 180° C. of between 1,000 and 20,000 mPa.s,
        (2) the pressure sensitive hot-melt adhesive is applied on the supporting material by means of gravure printing,
        (3) the patch material has a water-vapor permeability of more than 2,000 g/m²/24 h, and
        (4) the coat weight of the adhesive amounts to between 30 and 160 g/m².

2. The medical patch material according to claim 1 wherein the adhesive-free islands regularly arranged in the pressure sensitive hot-melt adhesive have a maximum distance of 3 mm to one another.

3. The medical patch material according to claim 1 wherein the base of the adhesive webs has a maximum width of 3 mm.

4. The medical patch material according to claims 1, 2 or 3 wherein the supporting material is a textile fabric.

5. The medical patch material according to claim 1 wherein the supporting material is a vapor-permeable film.

6. The medical patch material according to claim 1 which is an adhesive patch, a patch-type bandage, an adhesive dressing, a securing patch, an allergy-test patch, or a bacteria-proof wound dressing.

7. The medical patch material according to claim 6 which is sterilizable.

8. The medical patch material according to claim 1 wherein the proportion of the adhesive-free areas amounts to between 40 and 57% of the total surface.

9. The medical patch material according to claim 1 wherein the viscosity at 120° to 180° C. of the hot-melt adhesive is between 2,000 and 10,000 mPa.s.

10. The medical patch material according to claim 1 wherein the coat weight of the adhesive is between 40 and 120 g/m².

11. A process for the production of the medical patch material of claim 1 which comprises
    coating a support with a pressure sensitive hot-melt adhesive based on block copolymers having a viscosity at 120° to 180° C. of between 1,000 and 20,000 mPa.s by means of a heatable direct gravure print coater which uses both a rigid and an elastic coating knife in adhesive uptake in such a porous manner that the adhesive forms coherent webs in the longitudinal and transverse direction which include adhesive-free, island-shaped areas,
    the proportion of the adhesive-free areas amounting to between 30 and 60% of the total surface and the base of the adhesive webs having a maximum width of 3 mm, and
    the patch material having a water-vapor permeability of at least 3,000 g/m²/24 h.

12. A process according to claim 11 wherein the adhesive substance is applied on the support at a coat weight of between 30 and 160 g/m².

13. A process according to claim 1 wherein a block copolymer having a viscosity at 120°–180° C. of between 1,000 and 20,000 mPa.s, preferably between 2,000 and 10,000 mPa.s is used as adhesive.

14. A process according to claim 11 wherein the adhesive-free islands are regularly arranged in the pressure-sensitive hot-melt adhesive and have a maximum distance of 3 mm to one another.

15. A process according to claim 11 wherein the proportion of the adhesive-free areas amounts to between 40 and 57% of the total surface.

16. A process according to claim 12 wherein the coat weight is between 40 and 120 g/m².

* * * * *